(12) United States Patent
Nicolo

(10) Patent No.: US 6,652,595 B1
(45) Date of Patent: Nov. 25, 2003

(54) METHOD OF REPAIRING INGUINAL HERNIAS

(75) Inventor: Enrico Nicolo, Clairton, PA (US)

(73) Assignee: Davol Inc., Cranston, RI (US)

(*) Notice: Subject to any disclaimer, the term of this patent is extended or adjusted under 35 U.S.C. 154(b) by 0 days.

(21) Appl. No.: 09/488,724

(22) Filed: Jan. 9, 1998

Related U.S. Application Data (63) Continuation-in-part of application No. 08/621,475, filed on Mar. 25, 1996, now abandoned.

(51) Int. Cl.$^7$ .................................................. A61F 2/02
(52) U.S. Cl. .............................. 623/23.74; 623/23.72; 600/36; 606/51
(58) Field of Search ...................... 600/36; 606/151; 623/11.11, 23.74, 23.76, 23.72

(56) References Cited

U.S. PATENT DOCUMENTS

| 2,621,145 A | 12/1952 | Sano |
| 2,671,444 A | 3/1954 | Pease, Jr. |

(List continued on next page.)

FOREIGN PATENT DOCUMENTS

| CA | 2114282 | 7/1994 | |
| DE | 298 17 682 U1 | 4/1999 | |
| EP | 0 194 192 A1 | 9/1986 | |
| EP | 0 334 046 A2 | 2/1989 | |
| EP | 0 358 819 A1 | 3/1990 | |
| EP | 0537769 | 4/1990 | |
| EP | 0 719 527 A1 | 7/1996 | |
| EP | 0 560 934 | 8/1996 | |
| EP | 0 827 724 A2 | 3/1998 | |
| EP | 0 362 113 | 4/1999 | |
| FR | 2 744 906 A1 | 8/1997 | |
| GB | 1 352 282 | 6/1972 | |
| GB | 1 406 271 | 9/1975 | |
| SU | 1718857 | 3/1992 | |
| WO | WO 82/04390 | 12/1982 | |
| WO | WO 90/14796 | 12/1990 | |
| WO | WO 92/10218 | 6/1992 | |
| WO | WO 92/19162 | 11/1992 | |
| WO | 9317635 | 9/1993 | .................. 600/37 |
| WO | WO 94/17747 | 8/1994 | |
| WO | WO 96/09795 | 4/1996 | |
| WO | WO 96/14805 | 5/1996 | |
| WO | WO 97/35533 | 10/1997 | |
| WO | WO 98/14134 | 4/1998 | |
| WO | WO 00/07520 | 2/2000 | |

OTHER PUBLICATIONS

"Surgical—Multifilament yarn enhances surgical mesh flexibility": Elsevier Advanced Technology Publications: Jul. 1994: 1p.

Parviz K. Amid et al.: "Experimental evaluation of a new composite mesh with the selective property of incorporation to the abdominal wall without adhering to the intestines", Journal of Biomedical Materials Research, vol. 28, 373 375 (1994).

(List continued on next page.)

Primary Examiner—Paul B. Prebilic
(74) Attorney, Agent, or Firm—Wolf, Greenfield & Sacks, P.C.

(57) ABSTRACT

A universal, surgical prosthesis for hernia repair is provided in the form of a foldable sheet. The prosthesis includes a barrier layer formed of a material adapted to prevent biological adherence thereto, such as polytetrafluoroethylene, and a second surface layer formed of a material adapted to promote biological tissue adherence thereto, such as polypropylene. The second surface may be formed of a series of spaced projections. The prosthesis is adapted to be manipulated into an operative position to exhibit an appropriate exterior when in the operative position. In this manner, the universal, surgical prosthesis can be utilized for a wide range of surgical procedures.

16 Claims, 8 Drawing Sheets

U.S. PATENT DOCUMENTS

| | | | |
|---|---|---|---|
| 3,054,406 A | 9/1962 | Usher | |
| 3,272,204 A | 9/1966 | Artandt et al. | |
| 3,625,209 A | 12/1971 | Clark | |
| 4,051,848 A | 10/1977 | Levine | |
| 4,400,833 A | 8/1983 | Kurland | 623/13 |
| 4,576,608 A | 3/1986 | Homsy | |
| 4,585,458 A | 4/1986 | Kurland | |
| 4,633,873 A | 1/1987 | Dumican et al. | |
| 4,655,221 A | 4/1987 | Devereux | |
| 4,693,720 A | 9/1987 | Scharnberg et al. | |
| 4,725,279 A | 2/1988 | Woodroof | |
| 4,769,038 A | 9/1988 | Bendavid et al. | 623/13 |
| 4,854,316 A | 8/1989 | Davis | |
| 4,882,162 A | 11/1989 | Ikada et al. | |
| 4,942,875 A | 7/1990 | Hlavacek et al. | |
| 4,997,440 A | 3/1991 | Dumican | |
| 5,002,551 A | 3/1991 | Linsky et al. | |
| 5,007,916 A | 4/1991 | Linsky et al. | |
| 5,092,884 A | 3/1992 | Devereux et al. | |
| 5,100,422 A | 3/1992 | Berguer et al. | 606/151 |
| 5,104,400 A | 4/1992 | Berguer et al. | |
| 5,116,357 A | 5/1992 | Eberbach | |
| 5,116,360 A | 5/1992 | Pinchuk et al. | |
| 5,122,155 A | 6/1992 | Eberbach | |
| 5,141,515 A | 8/1992 | Eberbach | |
| 5,141,522 A | 8/1992 | Landi | |
| 5,147,374 A | 9/1992 | Fernandez | 606/151 |
| 5,147,401 A | 9/1992 | Bakker et al. | |
| 5,222,987 A | 6/1993 | Jones | |
| 5,254,133 A | 10/1993 | Seid | 606/216 |
| 5,258,000 A | 11/1993 | Gianturco | 606/151 |
| 5,290,217 A | 3/1994 | Campos | 600/37 |
| 5,292,328 A | 3/1994 | Hain et al. | 606/151 |
| 5,326,355 A | 7/1994 | Landi | 623/66 |
| 5,334,217 A | 8/1994 | Das | |
| 5,350,388 A | 9/1994 | Epstein | 600/37 |
| 5,356,432 A | 10/1994 | Rutkow et al. | |
| 5,366,460 A | 11/1994 | Eberbach | |
| 5,368,602 A | 11/1994 | de la Torre | 606/11 |
| 5,370,650 A | 12/1994 | Tovey et al. | 606/161 |
| 5,379,754 A | 1/1995 | Tovey et al. | |
| 5,425,740 A | 6/1995 | Hutchinson, Jr. | |
| 5,433,996 A | 7/1995 | Kranzler et al. | |
| 5,456,720 A | 10/1995 | Schultz | 600/37 |
| 5,461,885 A | 10/1995 | Yokoyama et al. | |
| 5,480,436 A | 1/1996 | Bakker et al. | 600/37 |
| 5,508,036 A | 4/1996 | Bakker et al. | |
| 5,519,004 A | 5/1996 | Urry | |
| 5,524,633 A | 6/1996 | Heaven et al. | 600/37 |
| 5,569,273 A | 10/1996 | Titone | |
| 5,593,441 A | 1/1997 | Lichtenstein et al. | |
| 5,601,579 A | 2/1997 | Semertzides | |
| 5,614,284 A | 3/1997 | Kranzler et al. | |
| 5,634,931 A | 6/1997 | Kugel | |
| 5,695,525 A | 12/1997 | Mulhauser et al. | |
| 5,697,978 A | 12/1997 | Sgro | |
| 5,716,408 A | 2/1998 | Eldridge et al. | |
| 5,716,409 A | 2/1998 | Debbas | |
| 5,722,992 A | 3/1998 | Goldman | |
| 5,725,577 A | 3/1998 | Saxon | |
| 5,733,337 A | 3/1998 | Carr, Jr. et al. | |
| 5,743,917 A | 4/1998 | Saxon | |
| 5,766,246 A | 6/1998 | Mulhauser et al. | |
| 5,769,864 A | 6/1998 | Kugel | |
| 5,813,975 A | 9/1998 | Valenti | |
| 5,916,225 A | 6/1999 | Kugel | |
| 6,258,124 B1 | 7/2001 | Darois et al. | |
| 6,270,530 B1 * | 8/2001 | Eldridge et al. | 623/23.74 |
| 2002/0052654 A1 | 5/2002 | Darois et al. | |

OTHER PUBLICATIONS

Goldstein Harold, M.D., F.A.C.S. atrium Polypropylene Mesh: "An Atlas of Hernia Repair Using an Inguinal Hernia Repair Preshape with Keyhole Slit"; Atrium Medical Corporation; Jun. 1996; 6 pp.

Robert G. Uzzo et al., "The Effects of Mesh Bioprosthesis on the Spermatic Cord Structures: A Preliminary Report in a Canine Model", The Journal Of Urology, Apr. 1999, vol. 161, pp. 1344–1349.

Gregory L. Brown, M.D. et al., "Comparison of Prosthetic Materials for Abdominal Wall Reconstruction in the Presence of Contamination and infections", Annals of Surgery, Jun. 1985, Vol 201, pps 705–711.

Scott D. Jenkins, M.D. et al., A Comparison of Prosthetic Materials Used to Repair Abdominal Wall Defects:, Surgery, Aug. 1983, vol. 94, No. 2, pps. 392–398.

Hernando Cordona, M.D., "Prosthokeratoplasty", 1983, Cornea, vol. 2, No. 3, 1983, pps 179–183.

Interceed(TC7) Adhesion Barrier Study Group (Cohen, Stephen M., et al.), Prevention of postsurgical adhesions by Interceed(TC7),*an absorbable adhesion barrier: a prospective, randomized multicenter clinical study, Fertility and Sterility, vol. 51, No. 6, Jun. 1989.

Alonzo P. Walker, M.D., James Henderson, D.V.M. and Robert E. Condon, M.D., "Double–Layer Prostheses for Repair of Abdominal Wall Defects in a Rabbit Model.", Jun. 1992.

* cited by examiner

METHOD OF REPAIRING INGUINAL HERNIAS

This is a continuation-in-part of U.S. patent application Ser. No. 08/621,475, filed Mar. 25, 1996, abandoned.

BACKGROUND OF THE INVENTION

1. Field of the Invention

The present invention relates to a mesh prosthesis. In particular, the present invention relates to a universal, surgical mesh prosthesis for hernia repair.

2. Description of the Prior Art

Surgical mesh prostheses of various different types have long been known and have long been used for hernia repair. The general surgical technique for hernia repair is to utilize a surgical mesh prosthesis, also called a hernia patch, over the hernia defect. The hernia patch has sufficient strength to resist the tendency of the hernia sack to protrude. The hernia patch is placed over the hernia defect and sutured to the surrounding tissue. This technique avoids undesirable, additional tension on the musculofascial tissue and minimizes the reoccurrence of a hernia.

Examples of hernia patches for hernia repairs can be found in U.S. Pat. Nos. 5,368,602; 5,356,432; 5,326,355; 5,292,328; 5,290,217; 5,254,133; and 5,147,374. Endoscopic and laparoscopic surgical techniques have been developed for repairing hernias with a hernia patch. Examples of these techniques can be found in U.S. Pat. Nos. 4,769,038; 5,379,754; and 5,370,650.

The hernia patches described in the prior art generally fall in two classes. The first class of hernia patch is formed of polypropylene material such as marketed by C. R. Bard, Inc. under the trademark MARLEX® or by United States Surgical Corporation under the trademark SURGIPRO®. A second class of hernia patch is mesh material formed of polytetrafluoroethylene (PTFE) such as marketed by W. L. Gore & Associates, Inc., under the trademark GORETEX®.

The two above-identified classes of hernia repair patches of the prior art each provide distinct advantages and disadvantages. The patches formed of polypropylene provide an excellent degree of tissue ingrowth for muscles and provide a sufficiently strong patch. However, the polypropylene hernia repair patches can result in unwanted adhesion of the abdominal viscera. When such adhesions occur, a "reopening" of the patient becomes increasingly difficult. The reopening of a patient in which unwanted adhesion occurred requires painstaking removal and separation of the abdominal viscera from the prosthetic material. Such a situation increases the danger of injury to the abdominal viscera as well as significantly increasing the length of the operation. As described in the above-noted patents, such reopenings are not uncommon in hernia operations.

The polytetrafluoroethylene (PTFE) hernia patches provide the advantage of minimizing or eliminating the adherence of the abdominal viscera to the hernia patch. The polytetrafluoroethylene hernia patches can easily be cut through without complications in a reopening procedure. However, the PTFE hernia patches are not as readily attachable to the muscle wall as the polypropylene meshes of the hernia patches described above. In view of the above discussion, it is clear that, in certain situations, the polypropylene hernia repair patches are better suited than the polytetrafluoroethylene hernia patches and vice versa for other applications. However, many applications find that none of the hernia patches of the prior art is entirely satisfactory.

U.S. Pat. No. 5,593,441 to Lichtenstein et al. addressed these drawbacks and provided a composite prosthesis for limiting the incident of postoperative adhesions. The composite included a mesh fabric with a barrier covering the mesh fabric to prevent exposure of the mesh fabric to areas of potential adhesion. The '441 patent discloses the use of polypropylene monofilament mesh fabric covered with a barrier layer, preferably formed of a sheet of silastic elastomer. The '441 patent contemplated replacing the silastic sheeting with microporous polypropylene sheeting, expanded PTFE, teflon mesh and oxidized, regenerated cellulose.

Parviz K. Amid and Irving L. Lichtenstein, coinventors on the '441 patent, followed the disclosures in the '441 application with an experimental evaluation of Lichtenstein's Journal of Biomedical Material Research Volume 28, pages 373–375 1994, entitled "Experimental Evaluation of New Composite Mesh with the Selective Property of Incorporation to the Abdominal Wall Without Adhering to the Intestines". This study included testing polypropylene mesh laminated (completely attached on the peritoneal side) with unreinforced vulcanize silastic sheeting, as well as testing polypropylene mesh attached on the peritoneal side to the polypropylene sheeting in such a way that the polypropylene mesh and the polypropylene sheeting between the attachment locations were left unattached to allow free infiltration of collagen fibrous from the host tissue into the polypropylene mesh. The results indicated a less than successful result with the polypropylene mesh completely attached on the peritoneal side with the unreinforced vulcanized silastic sheeting. The results also suggested that the composite structure should be formed as a layer of porous material on one side attached by a series of parallel lines to a layer of nonporous material on the intestinal side for tissue infiltration of the host tissue to one side and to prevent adhesions on the other.

The '441 patent as well as the composite prosthesis suggested in the Amid and Lichtenstein article, result in relatively complex and expensive manufacturing procedures.

SUMMARY OF THE INVENTION

The object of my present invention is to overcome the aforementioned drawbacks of the prior art. A further object of my invention is to provide a universal, surgical mesh prosthesis which is easily adapted for a wide variety of surgical procedures. A further object of my invention is to provide a surgical mesh prosthesis which is easy to utilize and cost effective to manufacture.

The objects of my invention are achieved by providing a universal, surgical mesh prosthesis in the form of a foldable sheet which is particularly well adapted for hernia repair. The prosthesis includes a barrier layer formed of a material adapted to prevent biological tissue adherence thereto and a second material coupled to and extending from one surface of the barrier layer, the second material formed of a material adapted to promote biological tissue adherence thereto. The second material projects from the one surface of the barrier layer at a series of spaced locations. The second material may be formed of a polyolefin such as polypropylene, and the barrier layer may be formed of a fluoropolymer such as polytetrafluoroethylene. The second material may be attached to the barrier layer by various techniques.

The sheet of my present invention is adapted to be manipulated to an operative position to exhibit between 0–100% of the second material on an exterior of the sheet when in the operative position.

Several specific examples of distinct operations utilizing the universal, surgical mesh prosthesis of my invention are disclosed. For example, my invention may be utilized in a ventral hernia operation wherein the second material is prevented from contacting the abdominal viscera by the barrier layer. The universal, surgical mesh of my invention is folded to an operative position in which the abdominal viscera is positioned adjacent the barrier layer while the second material is positioned adjacent the abdominal wall muscles. In this type of hernia operation, the barrier layer should not form a permanent layer to prevent adhesions. It is more effective if a neo-peritoneal layer forms over the prosthesis with the neo-peritoneal layer serving as a natural membrane to prevent adhesions to the prosthesis. The present invention is constructed in a manner to promote the growth of a neo-peritoneal layer. Further, my invention is also particularly well adapted for inguinal hernia operations in which the barrier layer is positioned adjacent the spermatic cord and the second material is positioned adjacent muscle tissue when in the operative position. The specific uses are intended to be only examples of the various types of distinct operations to which my universal hernia prosthesis is easily adapted.

These and other advantages of my present invention will be clarified in the brief description of the preferred embodiments taken together with the attached figures wherein like reference numerals represent like elements throughout.

BRIEF DESCRIPTION OF THE DRAWINGS

FIG. 9b is a sectional view of the prosthesis illustrated in FIG. 9a;

FIG. 10b is a sectional view of the prosthesis illustrated in FIG. 10a;

FIG. 10c is a sectional view of a modified version of the prosthesis illustrated in FIG. 10a;

FIG. 10d is a sectional view of a modified version of the prosthesis illustrated in FIG. 10a;

FIG. 11b is a sectional view of the prosthesis illustrated in FIG. 11a; and

BRIEF DESCRIPTION OF THE PREFERRED EMBODIMENTS

Figure 1:
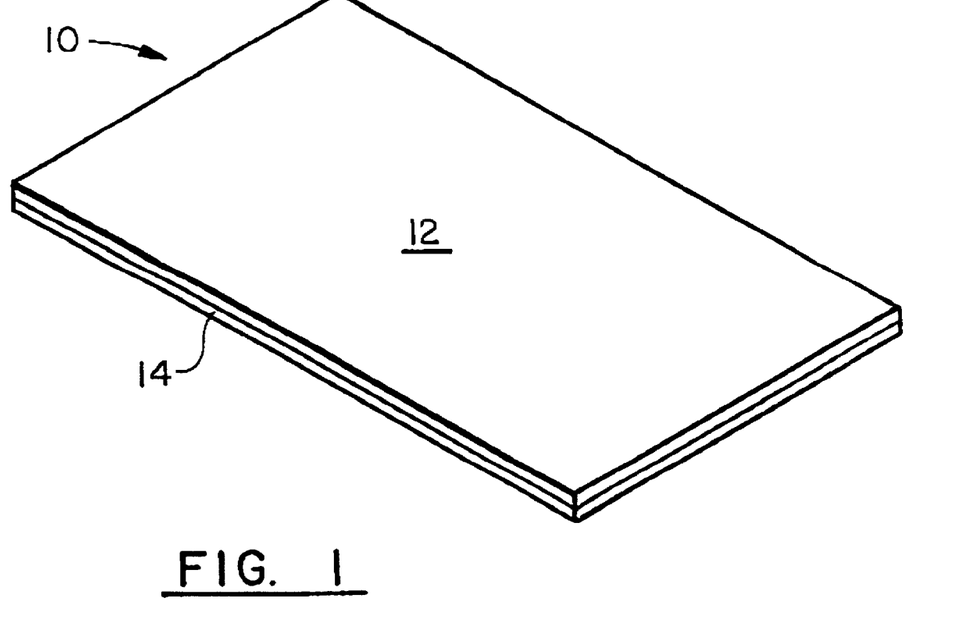
FIG. 1 is a perspective view of a universal, surgical mesh prosthesis according to my present invention.

FIG. 1 illustrates a universal, surgical mesh prosthesis 10 is in the form of a foldable sheet which is particularly well adapted for hernia repair. Consequently, the mesh prosthesis 10 is also referred to as a universal hernia patch. The mesh prosthesis 10 can be formed as a rectangular sheet, as shown in FIG. 1, in a large range of sizes. Additionally, the mesh prosthesis 10 may be preformed as circles, ellipses or any particular shape desired as demonstrated in FIGS. 6a–6c. Furthermore, the foldable mesh prosthesis 10 may be easily cut to the size needed for the particular operation. However, sizing the mesh prosthesis 10 appropriately to the more generally useful or utilized configurations, minimizes the trimming of excess material saving valuable operating time.

Figure 2:
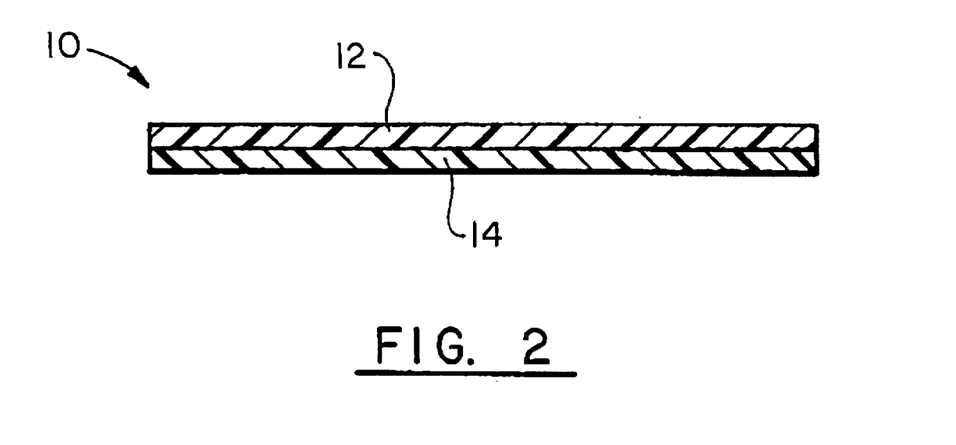
FIG. 2 is a cross section of the universal, surgical mesh prosthesis illustrated in FIG. 1.

As shown in FIG. 2, the mesh prosthesis 10 includes an outer layer 12 formed of a material adapted to promote biological tissue adherence thereto. The outer layer 12 promotes fibroplasis. The first outer layer 12 may effectively be formed of a polyolefin material such as polypropylene. Polyethylene also forms an acceptable polyolefin material for forming the outer layer 12. Easy availability of polypropylene together with its long history of acceptable use in surgical applications makes polypropylene a preferred material. Appropriate polypropylene material is sold under the trademarks MARLEX®, TRELEX NATURAL™ and SURGIPRO®.

A barrier layer 14 is coupled to and opposed from the first outer layer 12. The barrier layer 14 is formed of a material adapted to prevent biological tissue adherence thereto. The barrier layer 14 is formed to, at least temporarily, prevent fibroplasia. In certain hernia operations, it is preferred that the prosthesis 10 allows the growth of a neo-peritoneal layer over the barrier layer 14. In this construction, it will be the new neo-peritoneal layer, rather than the barrier layer 14, which prevents adhesions. The barrier layer 14 may be effectively formed of a fluoropolymer material such as polytetrafluoroethylene (PTFE). Fluorinated ethylene propylene (FEP), tetrafluoroethylene (TFE) and ethylene tetrafluoroethylene (ETFE) are other acceptable fluoropolymers. As with polypropylene discussed above, availability and acceptance in surgical applications make PTFE a generally preferred material for the barrier layer 14. Appropriate PTFE materials can be purchased under the brand names CORE-TEX® or TEFLON®. The barrier layer 14 may also be formed of a polyethylene terephthalate which is sold under the trademark DACRON® and MYLAR®.

The barrier layer 14 is attached directly to the first outer layer 12. The barrier layer 14 may be bonded to the outer layer 12 by known bonding techniques such as plasma treating or mechanical bridging through cornea treatment of the layers 12 and 14 in a gas environment. Thermobonding using heat and pressure or pressure bonding using pressure alone may be used in laminating-type techniques. Alternatively, the barrier layer 14 may be attached to the outer layer 12 by mechanical connection such as stitching or by use of a biologically inert adhesive.

One aspect of the present invention contemplates using an adhesive having a high shear strength such that the outer layer 12 and the barrier layer 14 are permanently attached together. An alternative aspect of the present invention is to select an adhesive with a relatively low shear strength which will provide two additional features. First, with a low shear strength adhesive, the outer layer 12 and the barrier layer 14 may be separated from each other prior to use if either the outer layer 12 or the barrier layer 14 is not desired for the specific surgical procedure being performed. Second, after the universal mesh prosthesis 10 is installed, the relatively low shear strength adhesive will provide some movement between the outer layer 12 and the barrier layer 14 relative to each other. However, the outer layer 12 and the barrier layer 14 would not become completely separated from each other in the operative position since, when installed, the surrounding portions of the surgical mesh prosthesis 10 will be secured to the surrounding biological tissue.

With the dual-sided universal, surgical mesh prosthesis 10, a number of surgical procedures can be addressed by simply folding the prosthesis 10 as needed.

Figure 3:
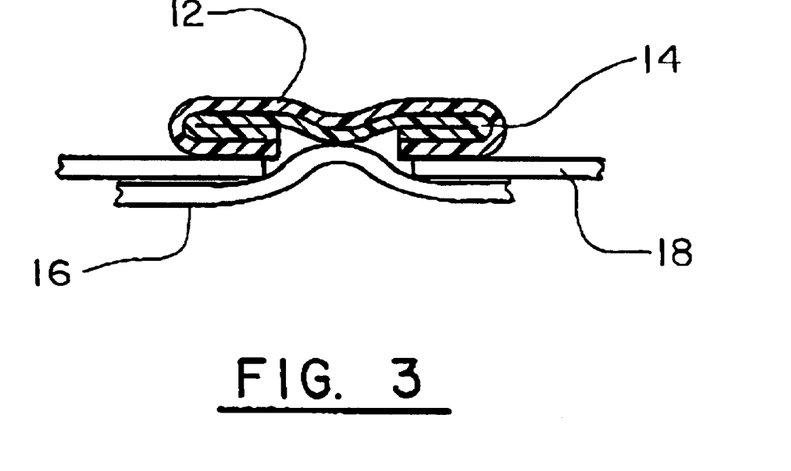
FIG. 3 schematically illustrates an operative position of the universal, surgical mesh prosthesis illustrated in FIGS. 1–2 in a ventral hernia operation.

FIG. 3 illustrates the surgical mesh prosthesis 10 utilized in a ventral hernia operation. In such an operation, it is preferable to prevent the abdominal viscera 16 from contacting the outer layer 12 which is adapted to promote biological tissue adherence thereto. It is advantageous to have the abdominal wall muscles 18 be positioned adjacent the outer layer 12 to promote the biological tissue adherence thereto. With these criteria in mind, the universal, surgical mesh prosthesis 10 is folded appropriately. In the operative position, the barrier layer 14 is essentially surrounded by the outer layer 12 on one side of the prosthesis 10. The other side of the prosthesis 10 in the operative position is formed entirely of the outer layer 12. The prosthesis 10 in the operative position is positioned over the hernia defect with the abdominal viscera 16 adjacent the barrier layer 14 and the abdominal wall muscles 18 adjacent the outer layer 12. The prosthesis 10 is attached to the biological tissue surrounding the hernia defect such as by stitching, stapling or other conventional means. Tissue adherence of the abdominal wall muscles 18 is promoted by outer layer 12. Tissue adherence of the abdominal viscera 16 is prevented initially by the barrier layer 14. Preferably, the prosthesis 10 allows a neo-peritoneal layer to be formed over the barrier layer 14. Following this formation, the neo-peritoneal layer will act naturally to prevent adhesions of the abdominal viscera to the prosthesis 10. As discussed above, adherence of the abdominal viscera 16 to a hernia patch would make later separation and follow-up work quite difficult.

Figure 4:
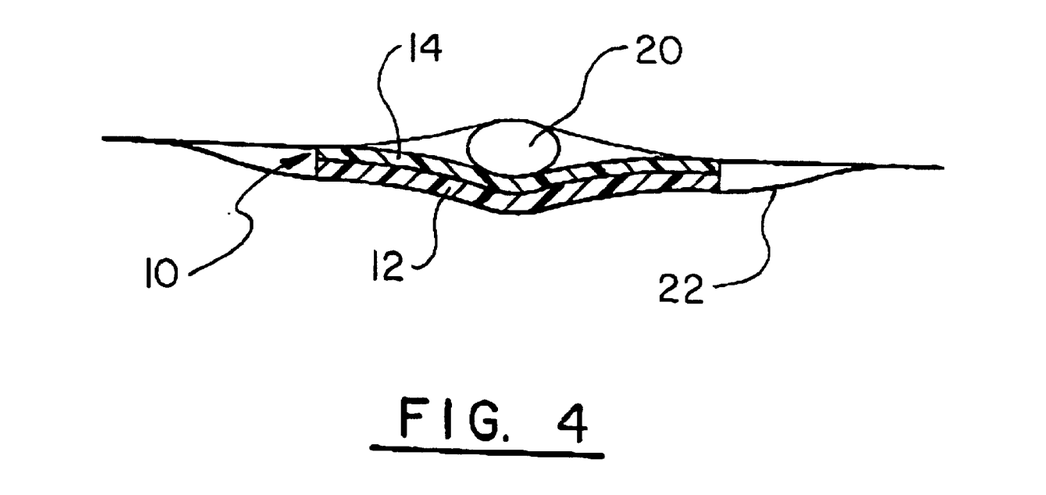
FIG. 4 schematically illustrates an operative position of the universal, surgical mesh prosthesis of FIGS. 1–2 in an inguinal hernia operation.

FIG. 4 illustrates the prosthesis 10 utilized in an inguinal hernia operation. In such inguinal hernia operations, the desired adhesion characteristics of the prosthesis 10 are substantially the opposite of the ventral hernia operation described above. In the inguinal hernia operation as shown, it is desired that the lower surface of the prosthesis 10 be biologically adherent. Consequently, in the inguinal hernia operation, the universal, surgical mesh prosthesis 10 is positioned in an operative position wherein the spermate cord 20 is positioned adjacent the barrier layer 14 and the outer layer 12 is positioned adjacent the muscle tissue 22 as shown. The prosthesis 10 is attached to the biological tissue surrounding the hernia defect by stitching or other conventional means.

The hernia operations described above are merely intended to be examples of the type of uses of the universal hernia patch of my invention. With the dual-sided hernia patch of my invention, a large number of operations can be performed utilizing a single type of patch. This will significantly reduce inventory requirements without adversely affecting performance.

Figure 5:
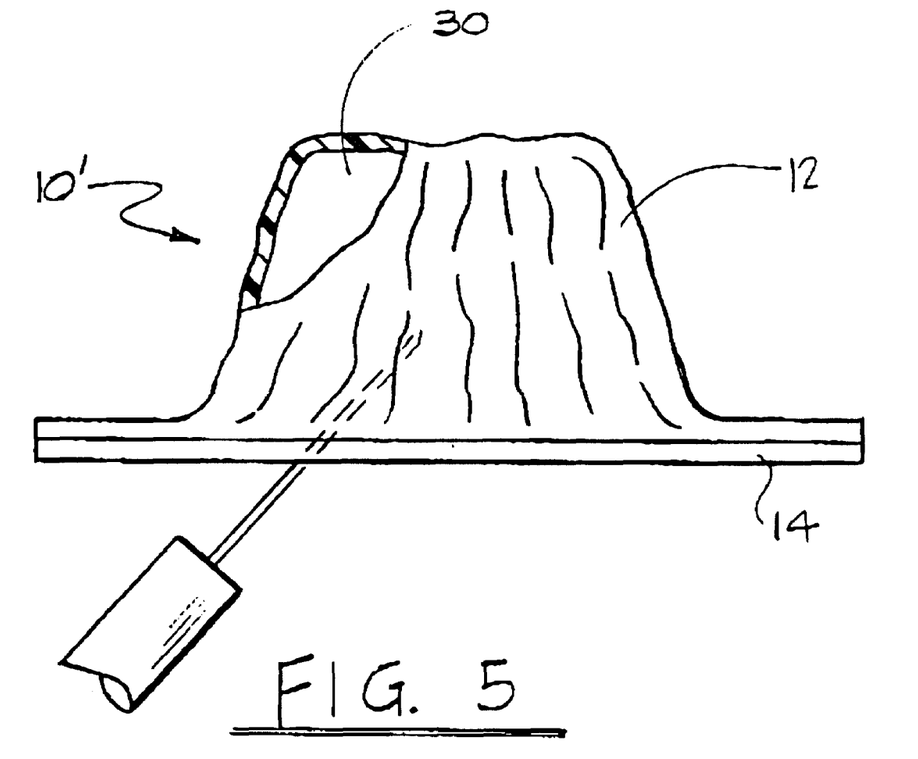
FIG. 5 is a side view, partially in section, of a modified universal, surgical mesh prosthesis according to my present invention.
Figure 7A:
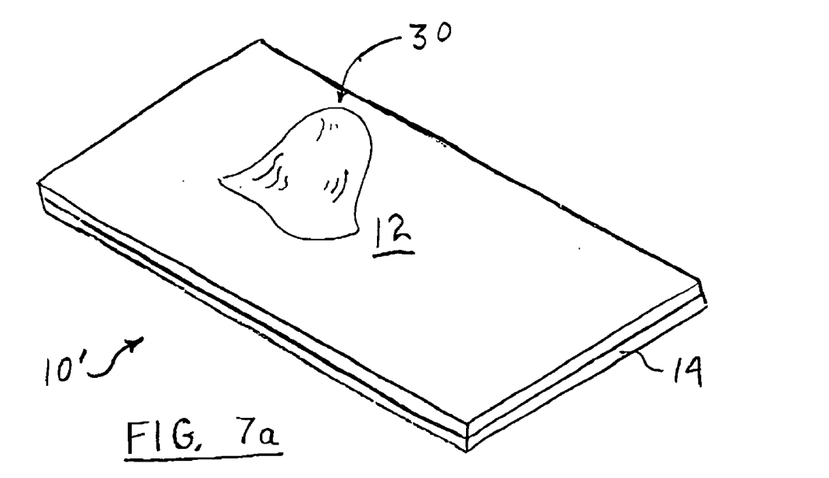
FIGS. 7a–7c illustrate various alternative shapes for the universal, surgical mesh prosthesis shown in FIG. 5.
Figure 7B:
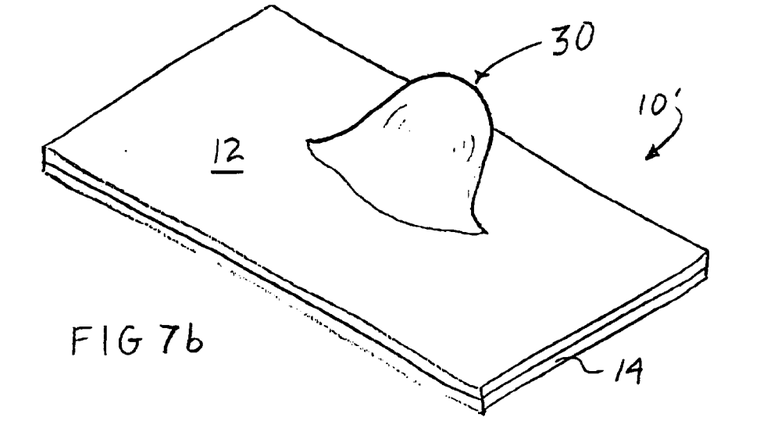
Figure 7C:
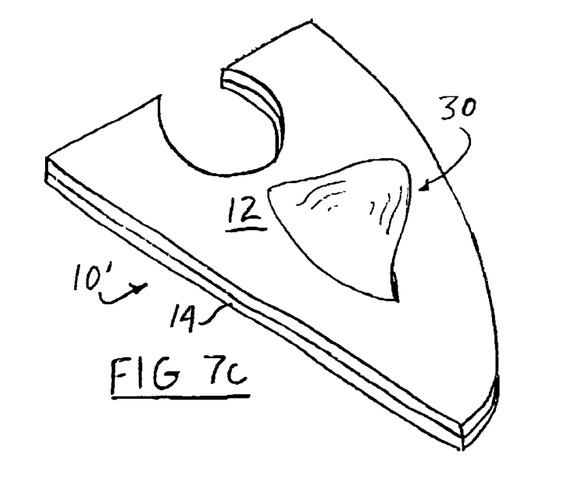

FIG. 5 schematically illustrates a modified surgical prosthesis 10' including an outer layer 12 and a barrier layer 14 formed of appropriate materials as described above in connection with prosthesis 10. The modified prosthesis 10' includes an expandable cavity 30 formed by outer layer 12 to form a plug member. The cavity 30, which is shown relatively large in FIG. 5 for ease of understanding, is specifically adapted to be placed into the hernia defect as a plug type of hernia prosthesis. When placed in the hernia defect, the cavity 30 may be filled with an inert gas or other appropriate inert material, such as saline, to expand and fill the hernia defect. The prosthesis 10' still maintains the advantages of the distinct layers 12 and 14 described above in connection with prosthesis 10. The prosthesis 10' is also foldable like the prosthesis 10 described above so that the appropriate exterior surface may be presented by the prosthesis 10' in the operative position. The prosthesis 10' may be formed by the user or preformed (i.e., manufactured) in a variety of usable shapes as shown in FIGS. 7a–7c. The placing of the plug member formed by the expandable cavity 30 within the hernia defect provides several distinct advantages. The cavity 30 will fill and provide support in the hernia defect whether or not the cavity 30 is subsequently filled. The insertion of the cavity 30 within the hernia defect will serve to anchor the prosthesis 10'. This may be particularly relevant where the prosthesis 10' is attached to the peritoneum overlaying the hernia defect. Without the cavity 30 extending into the hernia defect, relative movement could occur between the peritonea (to which the prosthesis 10' may be attached) and the hernia defect such that the hernia patch is no longer overlaying the hernia defect. The anchoring nature of the cavity 30 prevents unwanted migration, regardless of where the prosthesis 10' is attached. The cavity 30 will stimulate fibroplasia within the defect. Further, when the expandable cavity 30 is filled with filler, such as through use of an appropriately small gauge needle, as schematically shown in FIG. 5, the cavity 30 can be collapsed over time due to tissue contraction around the hernia defect, thereby minimizing the defect. The inert filler, such as saline fluid, displaced from the cavity 30 by tissue contraction will be harmlessly absorbed by the body. The prosthesis 10' combines the benefits of a hernia plug and a hernia patch and may reduce operating time.

Figure 6A:
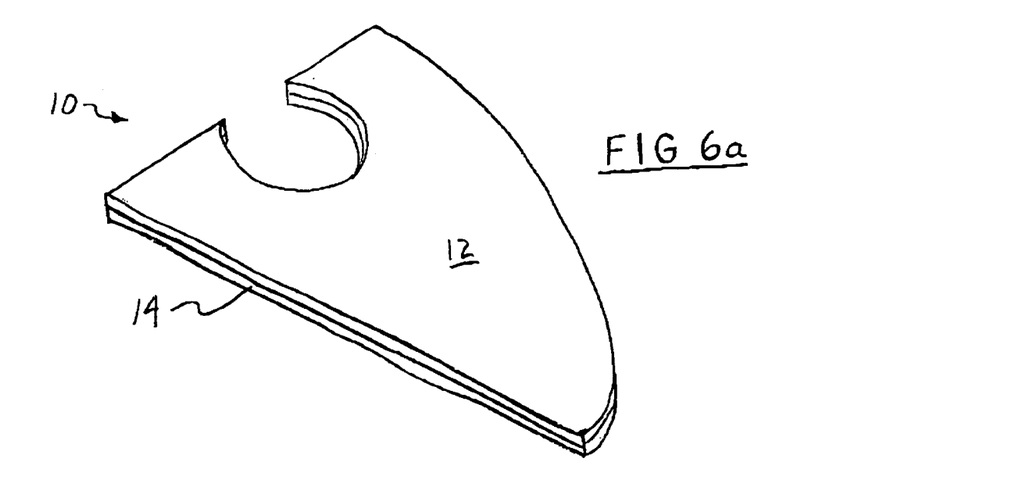
FIGS. 6a–c illustrate various alternative shapes for the universal, surgical mesh prosthesis shown in FIG. 1.
Figure 6B:
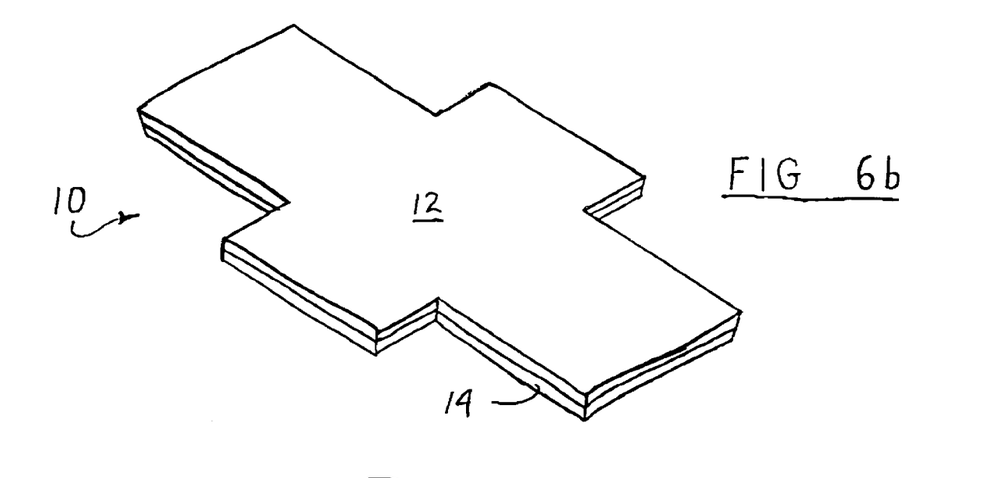
Figure 6C:
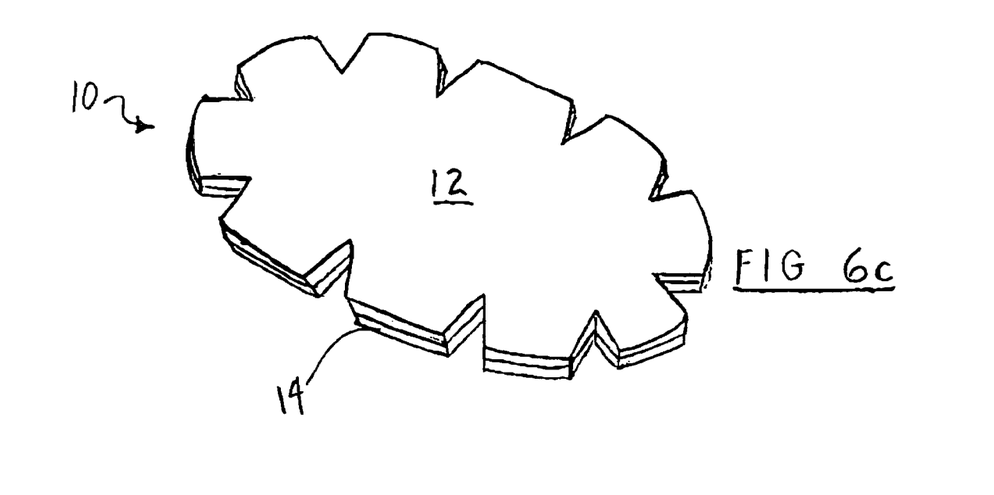

A summary of various hernia operations, in connection with both surgical mesh prosthesis 10 and 10' described above, will help clarify the versatility of my invention. In open (i.e., non-laparoscopic) inguinal hernia operations, the prosthesis 10 may be used in a general form as shown in FIG. 1 or preformed (i.e., manufactured) as shown in FIG. 6a. As discussed above, the user may form or shape the prosthesis 10 into any desired configuration. The preshaping of the prosthesis 10 as shown in FIGS. 6a–6c is merely intended to minimize additional forming/shaping steps by the user. The prosthesis 10' may also be used in open, inguinal hernia operations in a general non-preshaped form as shown in FIG. 7a or a preshaped form as shown in FIG. 7c. In the non-preshaped prosthesis 10' of FIG. 7a, the cavity 30 is preferably formed off-center to better accommodate the spermatic cord as will be recognized in the art. In laparoscopic inguinal hernia operations, the prosthesis 10 may be used in the general form shown in FIG. 1 or the prosthesis 10' may be used in the general non-preshaped form shown in FIG. 7b. For laparoscopic procedures, the cavity 30 of the prosthesis 10 no longer needs to be off-center as shown in FIG. 7a and may be positioned in the center of the prosthesis 30' as shown in FIG. 7b to maximize strength. For incisional hernia operations, the prosthesis 10 would be used either in the general form shown in FIG. 1 or with cutouts (formed or preformed) as shown in FIGS. 6b–6c to facilitate folding of the prosthesis 10 (similar to FIG. 3) without excess material. These examples are not exhaustive and are intended merely to demonstrate the wide variety of uses of my present invention.

Figure 8:
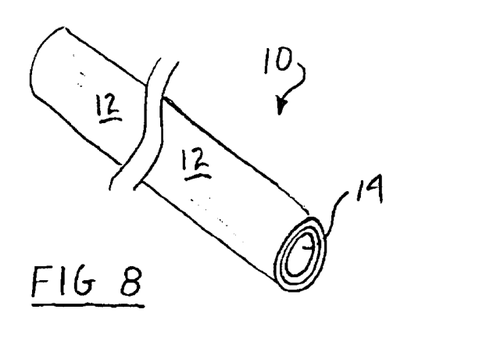
FIG. 8 illustrates a shape for the universal, surgical prosthesis shown in FIG. 1 which is specifically designed for vascular applications.

The prostheses 10 and 10' of my invention, while particularly well suited for hernia operations, are not specifically limited thereto and may have various other applications where a combination of biologically adherent and non-biologically adherent materials would be useful, such as thoracoplasty or in vascular surgery. For example, the prosthesis 10 of my invention as shown in FIG. 1 can be used for the reconstruction of the thoracic wall. The second outer layer 14, formed of PTFE or the like, will face the thoracic cavity. In vascular surgery, the prosthesis 10 may be preformed in a tubal fashion as shown in FIG. 8 where the inner surface of the tube is formed by the barrier layer 14 (PTFE or the like) and the outer surface of the tube is formed by the outer layer 13 (polypropylene or the like).

Another aspect of the present invention provides a universal surgical prosthesis which includes a barrier layer formed of a material adapted to prevent biological tissue adherence thereto and a plurality of spaced projections extending from one surface of the barrier layer. Each of the spaced projections are spaced from each other and are formed of a material adapted to promote tissue adherence thereto. As with the prosthesis discussed above, the barrier layer may not serve as a permanent barrier to prevent biological tissue adherence thereto. The prosthesis will preferably allow the formation of a neo-peritoneal layer overlaying the prosthesis such that the neo-peritoneal layer, rather than the barrier layer, acts in a natural manner to prevent adhesions.

Figure 9A:
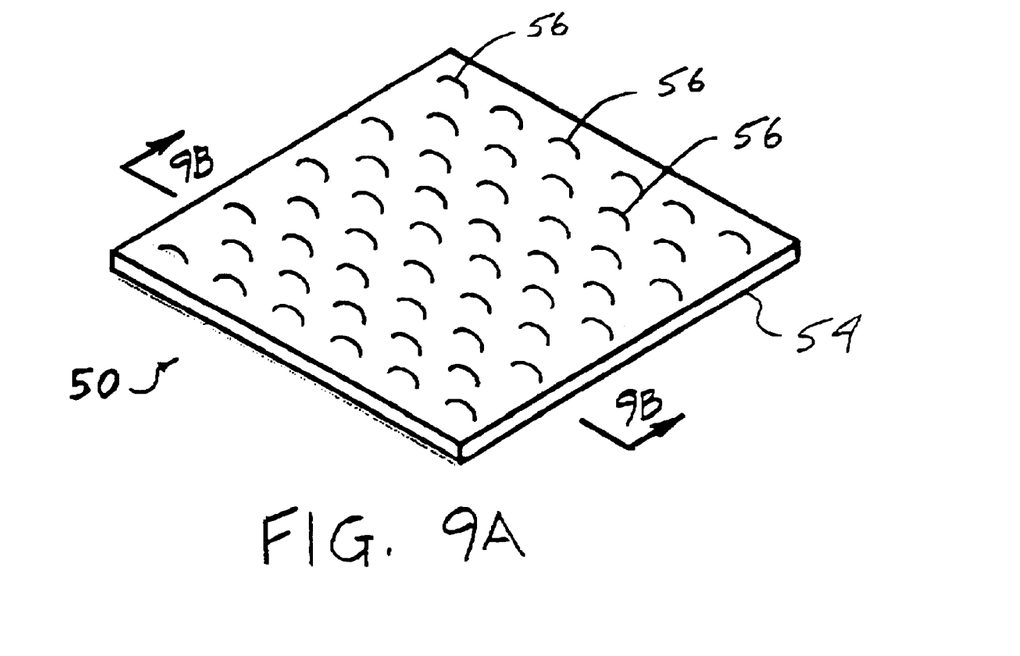
FIG. 9a is a perspective view of a surgical prosthesis according to another embodiment of my invention.
Figure 9B:
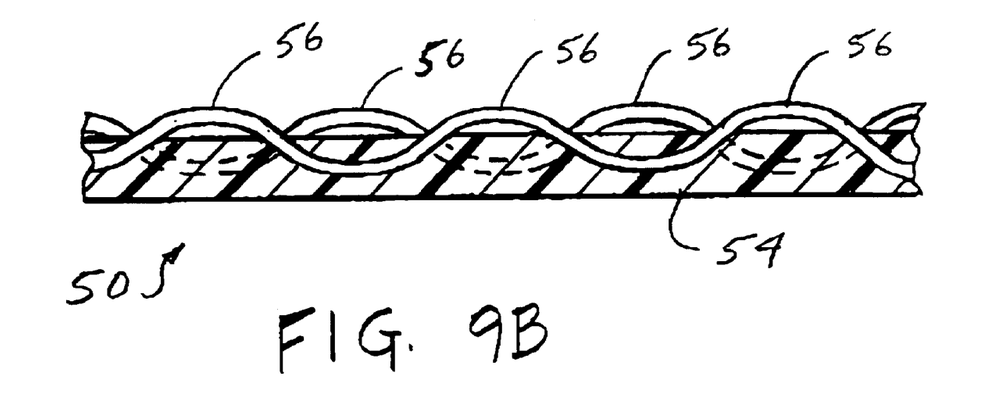

FIGS. 9a and 9b illustrate a prosthesis 50 according to a modified embodiment of the present invention. The prosthesis 50 includes a barrier layer 54 formed of a material adapted to prevent biological tissue adherence thereto, for example, PTFE. The barrier layer 54 is substantially similar to the barrier layer 14 described above. The prosthesis 50 includes a series of spaced projections 56 extending only from one surface of the barrier layer 54. The spaced projections 56 are spaced from each other as shown in FIG. 9a and are formed of a material adapted to promote tissue adherence thereto, for example, polypropylene. As better illustrated in FIG. 9b, the projections 56 can be formed of individual polypropylene monofilament strands stitched or woven into the barrier layer 54. As illustrated in FIG. 9b, the individual polypropylene monofilament strands are not stitched through the barrier layer 54 (i.e., they do not extend entirely through layer 54) and only extend partially in. Each stitch essentially forms one projection 56. The prosthesis 50 provides an easily manufactured prosthesis with the barrier layer 54 operating essentially the same as the barrier layer 14 described above and the surface of the barrier layer 54 including the projections 56 operating substantially the same as the surface of prosthesis 10 formed by outer layer 12. The surface of barrier layer 54 with projections 56 are intended to be utilized on a side where tissue incorporation is desired. In addition to easy manufacture of the projections 56, the prosthesis 50 illustrated in FIGS. 9a and 9b are intended to overcome the difficulties associated with the mesh prosthesis described in U.S. Pat. No. 5,593,441. Optionally, the prosthesis 50 provides the desired spacing between projections 56 while allowing space for tissue incorporation between the projections 56 and within each individual projection 56 as shown in FIG. 9b. Additionally, the prosthesis 50 eliminates the multiple layers with adhesion layers or the like therebetween. Consequently, this simple construction is believed to allow the formation of the neo-peritoneal layer which will ultimately serve as a natural barrier layer between the prosthesis 50 and the abdominal viscera.

Figure 10A:
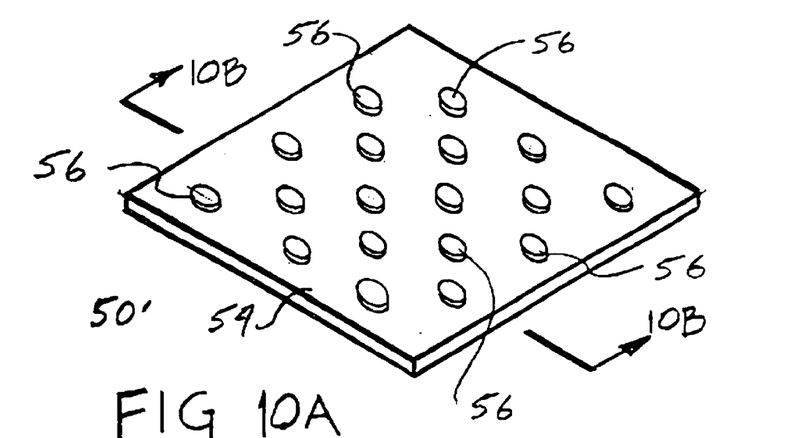
FIG. 10a is a perspective view of a surgical prosthesis according to another embodiment of my invention.
Figure 10B:
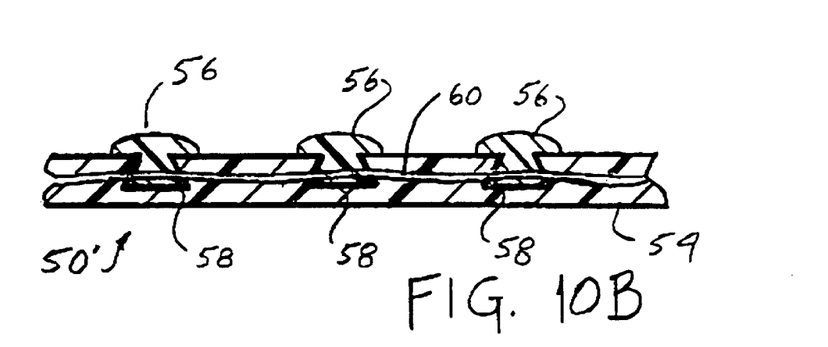
Figure 10C:
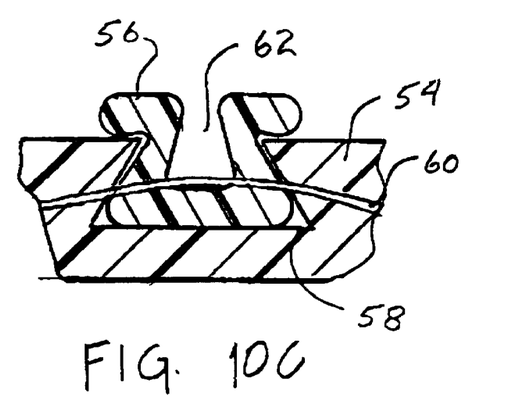
Figure 10D:
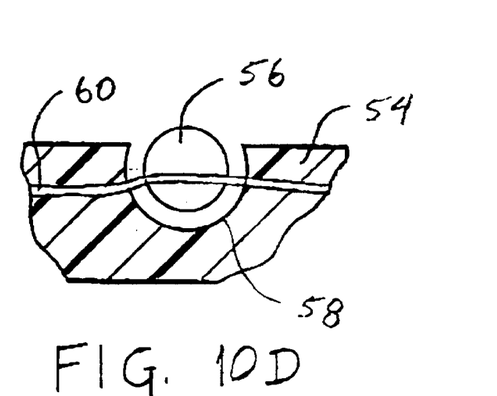

FIGS. 10a and 10b illustrate a prosthesis 50' according to another embodiment of the present invention. The prosthesis 50' is similar to the prosthesis 50 and includes a barrier layer 54 with a plurality of spaced projections 56 extending from one surface thereof. The barrier layer 54 is formed of a material adapted to prevent biological tissue adherence thereto, such as PTFE and the projections are formed of a material adapted to promote biological tissue adherence thereto, such as polypropylene. As shown in FIG. 10b, the projections 56 may be formed as individual plug members press fitted into recesses 58 formed on one surface of the barrier layer 54. As shown in FIG. 10b, the recesses 58 may be frusto-conical in shape such that when the plug members are pressed into the recess 58 the plug members will be locked into the recess 58 by the shape of the recess 58. The resiliency of the polypropylene material forming the plugs will allow the plug members to be inserted into the recess 58. Additionally, a locking strand 60 may extend through the recesses 58 and through the plug members to secure the plug members within the recesses 58. The locking strand 60 may be formed of a monofilament polypropylene strand. The plug members may be of any desired cross-section or shape which is found to promote tissue adherence thereto. For example, FIG. 10c shows a modified plug member which includes a central depression 62 formed in the plug member forming a projection 56. The inclusion of the depression 63 is intended to further promote tissue incorporation. FIG. 10d illustrates a further modified arrangement in which the plug member is loosely positioned within the recess 58 such that the locking strand 60 forms the primary mechanism for securing the plug member to the barrier layer 54. The loose fitting of the plug member within the recess 58 provides additional spacing therebetween to further assist in tissue incorporation. It is anticipated that these various designs may be further modified to provide the most easily assembled prosthesis which still provides the desired tissue incorporation on the side of the prosthesis including the spaced projections 56.

Figure 11A:
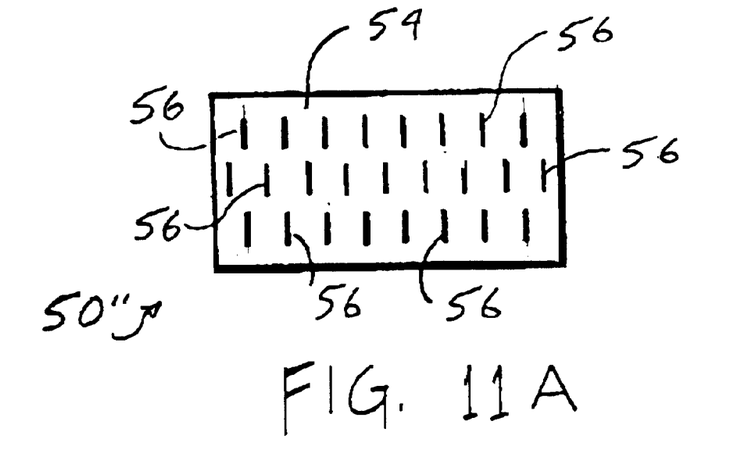
FIG. 11a is a plan view of a surgical prosthesis according to another embodiment of my invention.
Figure 11B:
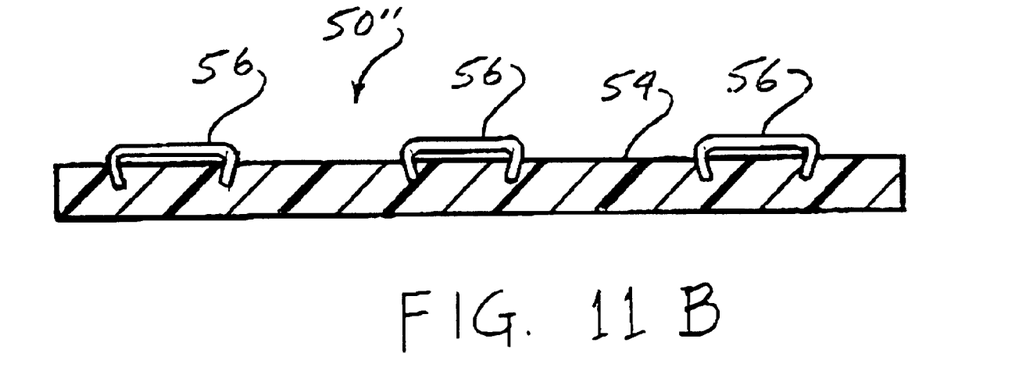

FIGS. 11a and 11b illustrate a prosthesis 50" similar to the prostheses 50' and 50 described above. Prosthesis 50" includes a barrier layer 54 formed of a material adapted to prevent tissue adherence thereto, such as PTFE. The barrier layer 54 is the same as barrier layer 54 as described above in connection with prosthesis 50 and 50'. Additionally, the prosthesis 50" includes a series of projections extending through one surface of the barrier layer 54 at spaced locations. The projections 56 are formed of a material adapted to promote biological tissue adherence thereto, such as polypropylene. In this embodiment, the projections 56 are formed as polypropylene staples in which the staples extend only partially into the barrier layer 54. The polypropylene staples may be formed as a metal body coated with polypropylene.

Figure 12:
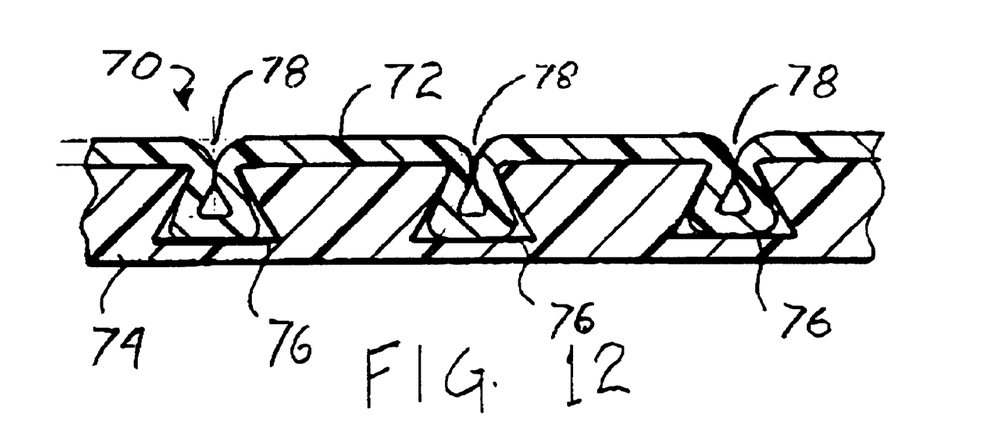
FIG. 12 is a sectional view of a surgical prosthesis according to another embodiment of my invention.

FIG. 12 illustrates a prosthesis 70 combining the aspects of prosthesis 10 and prosthesis 50 described above. Specifically, the prosthesis 70 includes an outer polypropylene layer 72 which is adapted to promote biological tissue adherence thereto and which is attached to a barrier layer 74 formed of PTFE to prevent biological tissue adherence thereto. Other materials may be substituted for the polypropylene and PTFE layers as discussed above. The polypropylene layer 72 is attached to the barrier layer 74 by press fitting portions of the polypropylene layer 72 into recessed grooves 76 to secure the polypropylene layer 72 thereto. The grooves 76 are shaped in a manner such that the sides are converged toward the opening on one side of the layer 76 such that when the polypropylene layer 72 is pressed therein, the polypropylene below the opening in the recess 76 will expand in the opening and secure the polypropylene layer therein as shown in FIG. 12. The pressing of the polypropylene layer 72 into the recesses 76 will form a depression 78 in the top surface of the polypropylene. In addition to providing an easy manufacturing method for attaching polypropylene layer 72 to the PTFE, it is believed that the depression 78 will further assist in tissue incorporation and will avoid the difficulties associated with the design found in U.S. Pat. No. 5,598,441. Additionally, it is anticipated that the set of grooves 76 extending across the barrier layer 74 may be formed or replaced with a plurality of spaced fructoconical recesses similar to the recesses 58 illustrated in FIG. 10*b*. These and other modifications may be readily apparent to those of ordinary skill in the art.

Although my invention has been described with particularity, it will be apparent to those of ordinary skill in the art that various modifications and changes may be made to my invention without departing from the spirit and scope thereof. Consequently, the scope of my invention is intended to be defined by the attached claims.

What is claimed is:

1. A method of repairing an inguinal hernia having a hernia defect within the inguinal canal, a spermatic cord structure being located within the inguinal canal, the method comprising:

providing a composite mesh having a first outer facing layer which is formed of a material adapted to promote biological tissue adherence thereto and a second outer facing layer formed of a material adapted to prevent biological tissue adherence thereto, said second outer facing layer being disposed on a surface of said first outer facing layer; and positioning said composite mesh to extend over the hernia defect with said first outer facing layer disposed between the hernia defect and said second outer facing layer and with said second outer facing layer disposed between said first outer facing layer and the spermatic cord structure to prevent adherence of the spermatic cord structure to the first outer facing layer.

2. The method of claim 1, wherein said composite mesh is provided with an opening adapted to receive the spermatic cord.

3. The method of claim 2, further comprising positioning the spermatic cord to extend through said opening in the composite mesh.

4. The method of claim 1, wherein said first outer facing layer is formed of polypropylene.

5. The method of claim 1, wherein said second outer facing layer is formed of PTFE.

6. The method of claim 1, wherein the first outer facing layer is formed as a sheet of material.

7. The method of claim 1, wherein the second outer facing layer is formed as a sheet of material.

8. The method of claim 1, wherein said second outer facing layer is formed of a fluoropolymer.

9. The method of claim 1, wherein said second outer facing layer is coupled to said first outer facing layer layer.

10. The method of claim 9, wherein said second outer facing layer is directly attached to said first outer facing layer.

11. The method of claim 9, wherein said second outer facing layer is bonded to said first outer facing layer.

12. The method of claim 11, wherein said second outer facing layer is thermo-bonded to said first outer facing layer.

13. The method of claim 9, wherein said second outer facing layer is attached to said first outer facing layer with a mechanical connection.

14. The method of claim 13, wherein said second outer facing layer is stitched to said first outer facing layer.

15. The method of claim 13, wherein said second outer facing layer is attached to said first outer facing layer with an adhesive.

16. The method of claim 15, wherein the adhesive has a low shear strength.

* * * * *